United States Patent
Li et al.

(10) Patent No.: US 7,794,666 B2
(45) Date of Patent: Sep. 14, 2010

(54) METHOD AND APPARATUS FOR CONTROLLING REACTION TEMPERATURE IN BIO-CHEMICAL INSTRUMENTS

(75) Inventors: William W. Li, Miami, FL (US); Rongchang Xin, Miami, FL (US); Wing S. Pang, Rowland Heights, CA (US); Dobson M. Okawa, Anaheim, CA (US)

(73) Assignee: Beckman Coulter, Inc., Brea, CA (US)

( * ) Notice: Subject to any disclaimer, the term of this patent is extended or adjusted under 35 U.S.C. 154(b) by 1236 days.

(21) Appl. No.: 11/349,445

(22) Filed: Feb. 7, 2006

(65) Prior Publication Data
US 2007/0183945 A1 Aug. 9, 2007

(51) Int. Cl.
G05D 23/00 (2006.01)
B01L 3/02 (2006.01)
B01J 19/00 (2006.01)

(52) U.S. Cl. .................. 422/109; 422/100; 422/129; 422/198

(58) Field of Classification Search ............. 422/109, 422/198, 100, 129; 164/47; 435/41, 289.1
See application file for complete search history.

(56) References Cited

U.S. PATENT DOCUMENTS

| 3,929,291 A | 12/1975 | Ladisch |
| 4,071,324 A * | 1/1978 | Reid ..................... 422/78 |
| 4,086,061 A * | 4/1978 | Hoffa et al. ............ 422/50 |
| 4,858,155 A | 8/1989 | Okawa et al. |
| 5,475,610 A | 12/1995 | Atwood et al. |
| 6,132,686 A * | 10/2000 | Gallup et al. .......... 422/130 |
| 6,258,323 B1 * | 7/2001 | Hormann et al. ....... 506/40 |
| 2002/0188196 A1 * | 12/2002 | Burbank et al. ........ 600/431 |
| 2003/0152492 A1 | 8/2003 | Chang et al. |

FOREIGN PATENT DOCUMENTS

JP 11165063 A * 6/1999

OTHER PUBLICATIONS

Machine translation of JP11-165063A, which was published Jun. 1999.*

* cited by examiner

*Primary Examiner*—Walter D Griffin
*Assistant Examiner*—Natasha Young
(74) *Attorney, Agent, or Firm*—Warren W. Kurz; Mitchell E. Alter

(57) ABSTRACT

Method and apparatus for controlling the temperature of one or more reaction vessels in a bio-chemical analyzer comprises a heat-exchange block, preferably made of cast aluminum or the like, and a thermoelectric device for heating or cooling the block to within a desired temperature range. The heat-transfer block cradles one or more reaction vessels in a thermal energy-transferring relationship, and further supports, in a thermal energy-transferring relationship, one or more fluid conduits serving to transmit a liquid or gas to the interior of the reaction vessels. Preferably, the heat-transfer block is cast from aluminum, and the fluid conduits are disposed inside the casting. By supporting the reaction vessel(s) and fluid conduit(s) in a common block, a single thermoelectric device and controller can be used to simultaneously control the respective temperatures of multiple fluid reagents and/or gases, as well as one or more reaction vessels, thereby reducing the power requirements of the thermal control system.

16 Claims, 4 Drawing Sheets

METHOD AND APPARATUS FOR CONTROLLING REACTION TEMPERATURE IN BIO-CHEMICAL INSTRUMENTS

BACKGROUND OF THE INVENTION

1. Field of the Invention

The present invention relates to improvements in apparatus for controlling the temperature of reactions in biochemical instruments such as, for example, hematology and blood-chemistry analyzers.

2. The Prior Art

In hematology and other blood-analyzing instruments, it is necessary to mix small volumes of a blood sample with specific diluents and/or liquid reagents in order to prepare the samples for subsequent analysis. For example, in hematology instruments, precise volumes of a whole blood sample are sequentially mixed with lysing and stable-lysing reagents in a reaction vessel to achieve a desired homogeneous and diluted concentration of lysed cells that is useful for a subsequent differential white cell analysis; similarly, precise volumes of a whole blood sample, a diluent and a lysing reagent are commonly mixed together to simultaneously dilute the sample and rid the sample of mature red cells in order to prepare the sample for a nucleated red blood cell analysis. In chemical analyzers, it is common to mix small volumes of blood serum with liquid reagents that change color in response to the presence of certain chemical elements or compounds of interest in the sample. In both types of instruments, it is always desirable to carry out the sample-preparation processes at or near an optimal temperature at which the desired results of the chemical reactions and/or the mixing of fluids associated with the sample-preparation processes can be readily achieved. Often, this optimal temperature approximates room temperature, say, about 75 degrees Fahrenheit (° F.). Since regulatory authorities specify that these instruments must be capable of operating satisfactorily within a relatively broad ambient temperature range, e.g., between 60 and 90° F., it is necessary to provide in such instruments some means for controlling the respective temperatures of both the reaction vessels and the samples and reagents in order to assure that sample-preparation is carried out at or near the selected optimal temperature.

In the commonly assigned U.S. Pat. No. 4,858,155 to Okawa et al., apparatus is disclosed for controlling the reaction temperatures in a chemical analyzer. Such apparatus operates to control the temperature of a plurality of reaction vessels or "cells" while simultaneously controlling the temperature of liquids that are fed to each cell without upsetting the temperature of the receiving cell. Such apparatus comprises multiple thermoelectric heating/cooling elements, some serving to individually heat or cool (depending on the ambient temperature) an individual reaction cell to a desired reaction temperature, and others serving to heat or cool individual conduits through which the fluid reagents are supplied to the reaction cells. To control the temperature of the reagents, the reagent conduits are coiled around a cylindrical "slug" of aluminum with which the thermoelectric heating/cooling element is thermally coupled. The coils are sized to hold at least the greatest selectable volume of fluid that is to be delivered to the reaction cells. Thus, upon being heated (or cooled) by the thermoelectric unit, the metal slug transfers (or removes) heat to (or from) the reagent conduits wrapped around it, as well as to the liquid therein. By this arrangement, the temperature of the reagents can be made to conform to a desired temperature before passage to a reaction cell. Meanwhile, control of the reaction cell temperature of a plurality of reaction cells is achieved by thermally coupling an independent thermoelectric heating/cooling element to each of a plurality of thermally-conductive containers to independently control the temperature of each container.

In the apparatus described above, the need for multiple thermoelectric heating/cooling devices to heat or cool the reagent conduits and each of the reagent containers renders the thermal control system relatively complex and costly to manufacture, calibrate and maintain.

SUMMARY OF THE INVENTION

In view of the foregoing discussion, an object of this invention is to provide a thermal control system of the above-type which requires but a single thermoelectric control to effect the selective and simultaneous heating or cooling of a reaction vessel and multiple fluid conduits by which different liquids and gases may be introduced into the reaction vessel.

Another object of this invention is to provide an improved apparatus for selectively and simultaneously controlling the respective temperatures of multiple reaction vessels and multiple fluid conduits serving to supply such vessels with the components necessary to prepare multiple liquid samples for subsequent analysis.

A preferred apparatus of the invention comprises (a) a block of thermally-conductive material, preferably made of aluminum, having a first cavity therein that is contoured to receive and support one or more reaction vessels so that the block is in intimate thermal contact with the side and/or bottom walls of at least a reaction chamber portion of the reaction vessel, and a second cavity that is adapted to support, in thermally-conducting relationship, one or more fluid conduits serving to supply liquids and/or gas to the reaction vessel; (b) a thermal sensor, preferably a thermistor, for sensing the temperature of the thermally-conductive block and for producing a control signal indicative of such temperature; and (c) a thermoelectric control device responsive to the control signal for selectively heating or cooling the thermally-conductive block to maintain the temperature of the thermally-conductive block at a desired temperature as fluids pass through the fluid conduit and enter the reaction chamber. Preferably, the thermally-conductive block supports multiple fluid conduits and multiple reaction vessels. It is further preferred that the block is made of cast aluminum, and that the conduits are made of a durable and highly heat-conductive metal, such as stainless steel, and the conduits are integrated into the interior of the block during a casting process by which the block is formed.

By virtue of the invention, the temperatures of several reagents and reaction chambers can be controlled by a single thermoelectric unit. Further, as explained below, by spreading the cooling or heating load through the energy storage capacity of the block, the power requirement to the thermoelectric device is minimized. Still further, the compactness of the structure results in high energy efficiency.

The invention and its various aspects and advantages will be better understood from the ensuing detailed description of preferred embodiments, reference being made to the accompanying drawings in which like reference characters denote like parts or components.

DETAILED DESCRIPTION OF PREFERRED EMBODIMENTS

Figure 1:
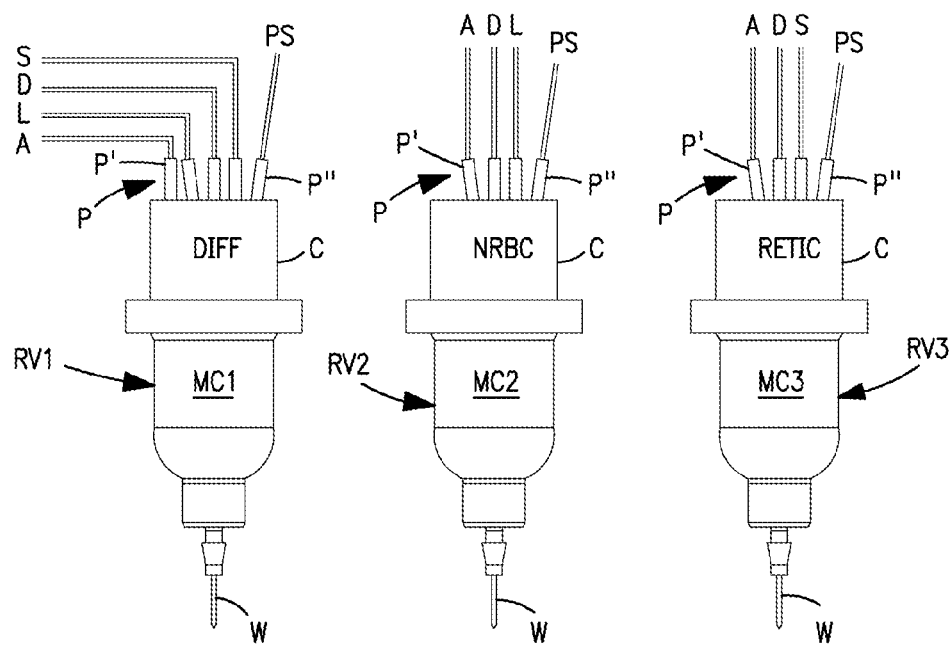
FIG. 1 illustrates a plurality of reaction vessels of the type used in hematology instruments.
Figure 2:
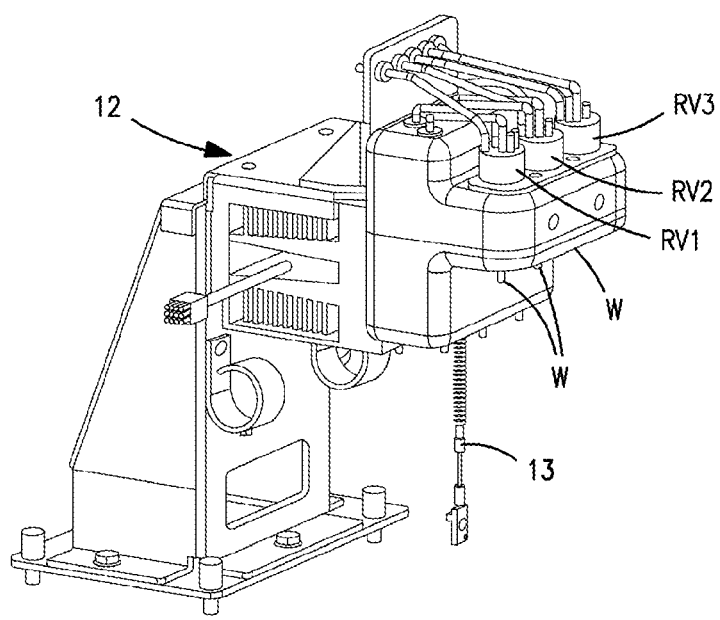
FIG. 2 is a perspective illustration of a portion of a hematology instrument embodying the invention.
Figure 3:
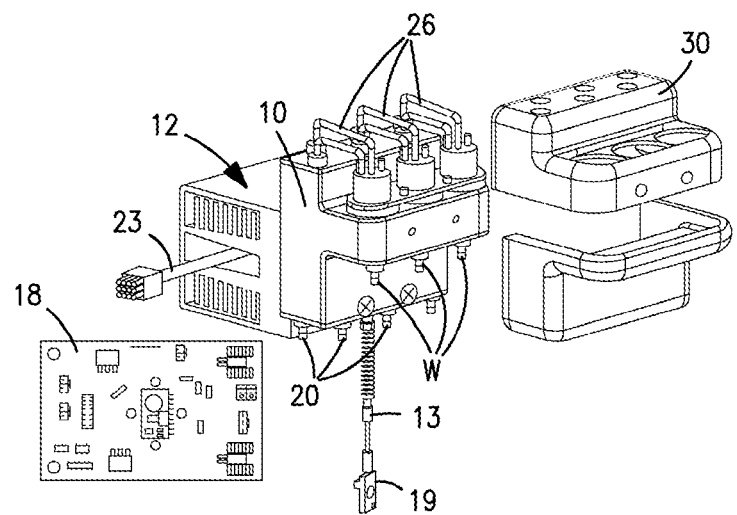
FIG. 3 is an exploded view of the FIG. 2 apparatus.
Figure 7:
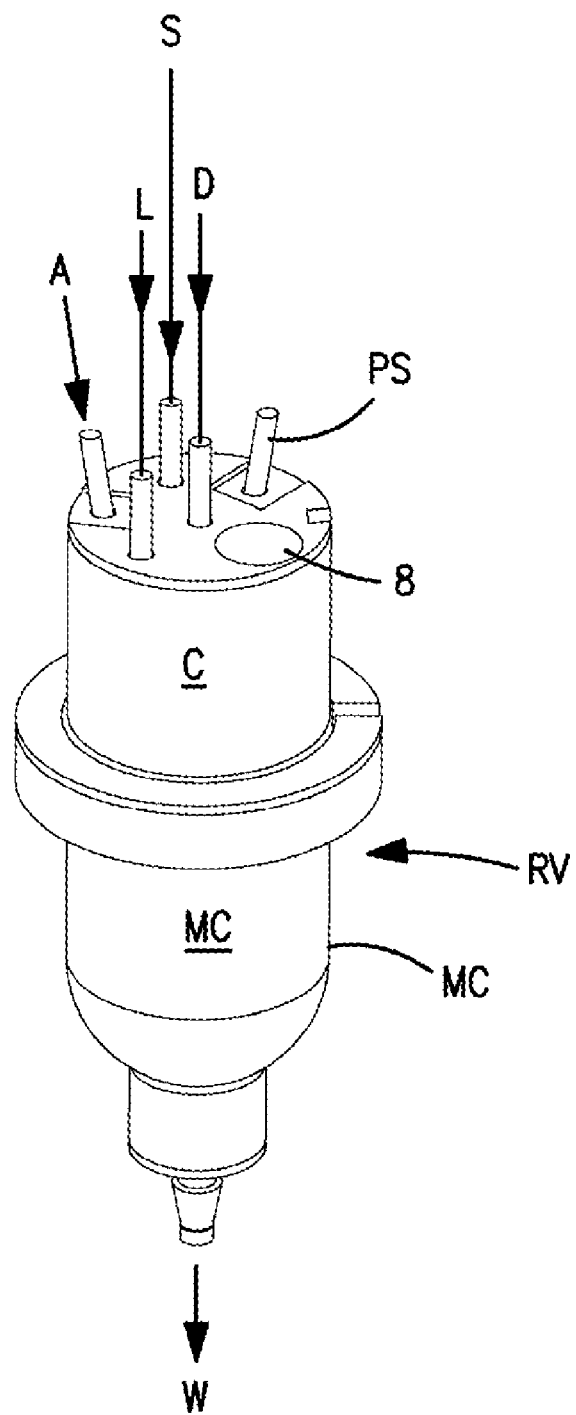
FIG. 7 is a perspective illustration of a reaction vessel of the type used with the apparatus of the invention.

Referring now to the drawings, FIG. 1 illustrates a plurality of reaction vessels RV1-RV3 of the type used in a hematology instrument to prepare blood samples for analysis. Each reaction vessel defines an enclosed mixing chamber portion (shown as MC1-MC3) and comprises a cap C that encloses the underlying mixing chamber. Each cap supports one or more input ports P through which various reagents (e.g., lyse L, stabilyse S and diluent D) may be introduced into the mixing chambers. Each vessel further comprises a port P' through which pressurized air A may be selectively directed at the contents of the mixing chamber to effect homogeneous mixing of the reagents with the sample therein, and an opening 8 formed in the top of the vessel (best shown in FIG. 7) through which a blood sample may be dispensed into the mixing chamber for mixing with the reagent(s). Following preparation of the blood sample in the mixing chambers, the prepared sample PS may be transferred from the reaction vessel through a port P". While the prepared sample is analyzed, each mixing chamber is cleansed with a diluent, and the effluent is removed through a waste port W. In FIG. 1, the three reaction vessels RV1-RV3 are respectively illustrated as being used to prepare blood samples for Differential White Cell analysis (DIFF), nucleated red blood cell (NRBC) analysis, and reticulocyte (RETIC) analysis.

As noted above, hematology instruments and similar biochemical analyzers are commonly designed to operate throughout a relatively wide range of ambient temperatures, e.g., between 60 and 90° F. But the temperature at which the reagents best react with the blood sample is, by design, about normal room temperature, e.g., 75+/−3° F. Thus, when the instrument ambient temperature is outside the best reaction temperature range, it is highly desirable to either cool or heat the reagents and/or reaction vessels so as to maintain the desired reaction temperature.

Figure 4:
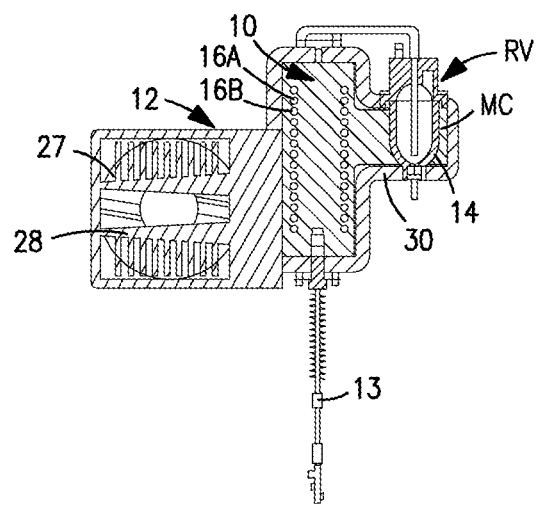
FIG. 4 is a cross-sectional illustration of the FIG. 2 apparatus.
Figure 5:
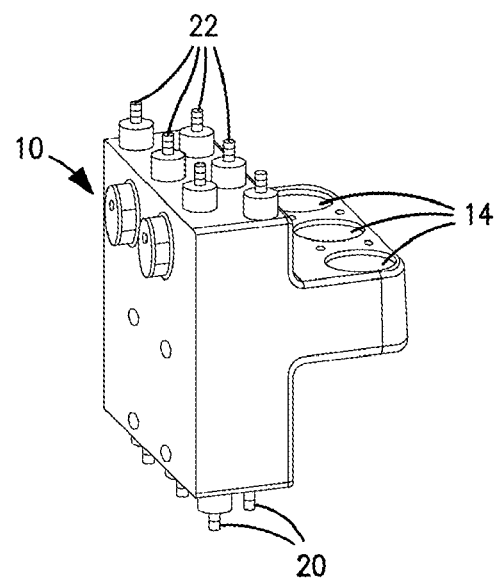
FIG. 5 is a rear-perspective view of the heating/cooling block of the FIG. 2 apparatus.

In FIGS. 2-5, apparatus for selectively heating or cooling the respective temperatures of a plurality of reaction vessels, as well as the reagents supplied thereto, in instruments of the type noted above is shown as comprising a thermally-conductive heat-exchange block 10, shown best in FIG. 5. Such apparatus further comprises a thermoelectric heating/cooling device 12 that operates under the control of a microprocessor-based controller 18 to control the temperature of block 10 in response to the output of a temperature sensor 13, such as a thermistor, having a connector 19 that, in use, is operatively connected to controller 18. Sensor 13 is thermally coupled to the block 10 and continually produces an output signal reflective of the instantaneous temperature of the heat-exchange block. Preferably, the block 10 is fabricated from a solid piece of metallic material of high thermal conductivity and, most preferably, it is casted from an aluminum or copper alloy. As best shown in FIGS. 4 and 5, block 10 defines a plurality of reaction vessel-receiving cavities 14, each being contoured to receive and cradle in thermal-energy-transmitting relationship, at least the mixing chamber portion MC of a reaction vessel RV. Thus, by controlling the temperature of block 10, the temperature of all three reaction vessels (in the embodiment shown) are simultaneously controlled by the transmission of thermal energy between the block and the mixing chamber of each reaction vessel.

Figure 6:
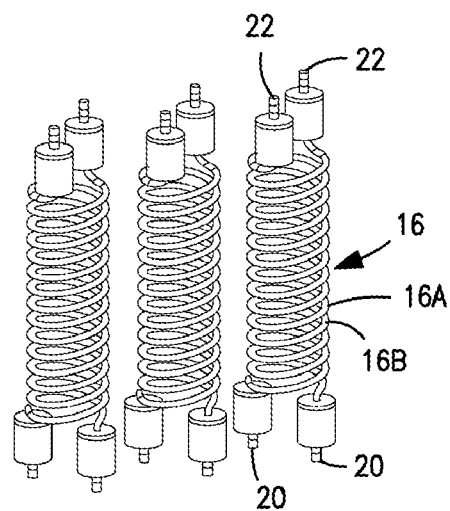
FIG. 6 is a perspective view of the coiled reagent conduits that are supported within the heating/cooling block illustrated in FIG. 5.

As best shown in FIGS. 3-6, the heat-exchange block 10 further functions to support and to transfer thermal energy to a plurality of fluid conduits 16 by which sample and reagent fluids are dispensed into the reaction vessels for mixing. These conduits further serve to transmit pressurized gas, e.g., air, used to provide air jet-mixing of the substances within the mixing chambers of the reaction vessels. In FIG. 6, three pair of such conduits are shown, each pair comprising first and second individual conduits 16A and 16B that are spirally wound and interdigitated with respect to each other. The interdigitation serves to conserve the space needed within block 10 to transfer thermal energy to the conduits, and the spiral winding effectively extends the length and heat-transfer area of each conduit and the heat-exchange capacity between the conduit and fluid passing from the entrance coupling 20 of each conduit to the exit coupling 22 thereof. Preferably, each of the conduits 16A and 16B is made of stainless steel, and each is embedded in the casted aluminum block, as indicated in FIG. 4, whereby excellent heat transfer is provided between the block and the fluid within the conduits. Such embedding of the fluid conduits in block 10 can be achieved by positioning the conduits in a mold that defines the exterior shape of block 10 prior to pouring molten aluminum into the mold. The conduits may be made of any material having a melting temperature substantially higher than that of the block material and which does not chemically react with the block material. Stainless steel is preferred.

The thermoelectric control device 12 serves, in a conventional manner, to vary the temperature of the heat-exchange block 10 as needed to adjust the temperature of the reaction vessels and fluids supplied thereto. Such a device is commercially available, and a preferred thermoelectric control device may be obtained from Supercool U.S. Inc. The functions of the heat-exchange block 10 include: storing or removing heat energy from thermoelectric device 12, transferring or absorbing heat energy to or from the liquid reagents or air carried by the fluid conduits, and providing a temperature controlled local surrounding for the reaction chambers of the reaction vessels. The block-temperature sensor 13 is mounted on the heat-exchange block 10 and connected to a control board 18 through a connector 19. Through a cable 23, the control board supplies the power to the thermoelectric module 12 and to a fan 27 that controls the temperature of a heat sink 28, both being located within the thermoelectric device 12.

The control board functions to monitor the output of the heat-exchange block temperature sensor 13, and adjusts the power to the thermoelectric device 12 accordingly. It further operates to automatically switch the polarity of the DC power input to thermoelectric device, thereby switching between heating and cooling modes of the system, depending on the ambient temperature. The reagent supply lines (not shown) are connected to the input fittings 20 of the helically-wound fluid conduits 16, as best shown in FIG. 6, such fittings being located beneath the heat transfer block 10. The liquid reagents and air flow through the helical conduits 16 which are connected to the input ports P of the reaction chambers by the bridging tubes 26 and the output fittings 22 located atop the heat-exchange block 10. The control board 18 is powered by the instrument's main power supply, and the control parameters are suitably programmed in the control board or instrument computer. A thermal insulation housing 30 is positioned around block 10 and functions to minimize the energy loss from the system to ambient to increase the energy efficiency.

The thermal control process begins when the instrument is turned on. The control board 18 reads the temperature sensor 13 which reflects the temperature of the heat-exchange block. If the temperature is higher than the setting point (for example, 75° F.), the control board supplies DC power with a polarity such that the thermoelectric device operates in its cooling mode. The heat-exchange block temperature thus decreases. When the block temperature reaches a level within a range near the setting point (75+/−3° F.), the system operates in a proportional control phase such that the input current of the thermoelectric device is proportional to the difference between the block temperature and the setting point. During sample preparation, as the reagents flow through the conduits, they are cooled down to a level proximate the block temperature at the ends of the helical coils by transferring heat from the block. In the same time, the block temperature may increase, so the input power of the thermoelectric device will increase, and remove more heat from the block in order to maintain the block temperature close to a desired setting point. The control performance depends on the correct selection of the thermoelectric device power, the reagent consumption rates, the helical coil size of the fluid conduits, and the heat capacity of the heat-exchange block. In the implemented embodiment, the block temperature has been shown to remain in the range of 75+/−2° F. The reaction chamber bodies are enclosed in the heat-exchange block, so their surrounding temperatures remain in the same temperature range as the block temperature. When the ambient temperature is lower than the setting point, the system will operate in the heating mode in a similar heat-exchange process.

The heat capacity of the heat-exchange block plays important roles in the process and performance of the system. First, it works as an energy reservoir. Since the energy for cooling or heating the reagents does not directly from the thermoelectric device, so it greatly reduces the peak demand to the thermoelectric device. Second, it works as a stabilizer. The higher the heat capacity ratio of the heat-exchange block to the reagent consumption, the less is variation of the block temperature.

To account for different heat-transfer coefficients of the various fluid substances (including the jet-mixing air) passing through block 10, the length of the conduits may be altered, some conduits having more coil turns than others. Alternatively, some fluids, e.g., air, which has a relatively low heat-transfer coefficient, may be passed through plural conduits that have been connected in series by suitable bridging conduits, while other fluids, e.g., diluent that is usually provided to the reaction vessels in relatively large volume, may be passed through plural conduits simultaneously, in which case these conduits are connected in parallel to a diluent supply source and to a desired reaction chamber.

The invention has been described with reference to certain preferred embodiments. Clearly, variations can be made without departing from the spirit of the invention, and such variations are intended to fall within the scope of the appended claims.

What is claimed is:

1. Apparatus for controlling the reaction temperature of different substances mixed together in one or more reaction vessels, said apparatus comprising:

(a) a heat-exchange block comprising a thermally-conductive material, said block defining (i) one or more first cavities, each being contoured to receive and support a reaction vessel so that the block is in intimate thermal contact with a side and/or bottom wall of said reaction vessel, and (ii) a plurality of second cavities, each being contoured to receive and support a conduit for introducing a substance into said reaction vessel, said conduit being received and supported by said second cavity so that said block is in intimate thermal contact with a portion of a side wall of said conduit, said thermally-conductive block being made by a casting process in which molten metal is poured into a mold that is shaped to define said first and second cavities;

(b) a thermal sensor for sensing the temperature of the thermally-conductive block and for producing a control signal indicative of such temperature; and (c) a thermoelectric control device responsive to the control signal for heating or cooling the thermally-conductive block to maintain the temperature of the thermally-conductive block at a temperature adapted to maintain the respective temperatures of said reaction vessel and substances passing through said conduit and entering said reaction vessel within a desired reaction temperature range.

2. The apparatus as defined by claim 1 wherein at least one of said conduits is spiral in shape.

3. The apparatus as defined by claim 1 wherein a jet of pressurized gas is used to mix said substances within said reaction vessel, and wherein said gas is introduced into said reaction vessel through one or more of said conduits, whereby the temperature of said pressurized gas is controlled by said thermoelectric control device.

4. The apparatus as defined by claim 1 wherein a plurality of conduits are connected in series, and selected substances are passed through said plurality of conduits sequentially to control the temperature thereof.

5. The apparatus as defined by claim 1 wherein a plurality of conduits are connected in parallel, and selected substances are passed through said plurality of conduits simultaneously to control the temperature thereof.

6. The apparatus as defined by claim 1 wherein some of said conduits with said block are longer than others, whereby the respective temperatures of substances having different heat-exchange characteristics can be controlled.

7. The apparatus as defined by claim 1 wherein said thermally-conductive block is made by a casting process in which molten metal is poured into a mold that is shaped to define said first cavity, and wherein the shape of said second cavity is defined by independent conduits that are positioned within said mold during said casting process, said conduits being made of a second metal having a higher melting temperature than the metal from which said block is cast.

8. The apparatus as defined by claim 7 wherein said molten metal comprises aluminum, and wherein said second metal comprises stainless steel.

9. The apparatus as defined by claim 7 wherein said conduits have a helical shape.

10. A method for controlling the reaction temperature of different substances mixed together in a reaction vessel, said apparatus comprising:

(a) providing a heat-exchange block of thermally-conductive material, said block defining (i) a first cavity therein that is contoured to receive and support said reaction vessel so that the block is in intimate thermal contact with a side and/or bottom wall of said reaction vessel, and (ii) a second cavity that is adapted to support, in thermally-conducting relationship, a plurality of conduits for introducing substances into said reaction vessel;

(b) positioning said reaction vessel in said first cavity of said block and positioning said conduits in said second cavity of said block so that said reaction vessel and said conduits are in intimate thermal contact with said block;

(c) passing substances through said conduits and into said reaction vessel;

(d) sensing the temperature of the thermally-conductive block and producing a control signal indicative of such temperature; and (e) in response to said control signal, heating or cooling the thermally-conductive block to maintain the temperature of the thermally-conductive block at a temperature adapted to maintain the respective temperatures of said reaction vessel and substances passing through said conduit and entering said reaction vessel within a desired reaction temperature range.

11. The method as defined by claim 10 wherein said thermally-conductive block supports multiple reaction vessels.

12. The method as defined by claim 10 wherein a jet of pressurized gas is used to mix said substances within said reaction vessel, and wherein said gas is introduced into said reaction vessel through one or more of said conduits, whereby the temperature of said pressurized gas is controlled.

13. The method as defined by claim 10 wherein a plurality of conduits are connected in series, and selected substances are passed through said plurality of conduits to control the temperature thereof.

14. The method as defined by claim 10 wherein a plurality of conduits are connected in parallel, and selected substances are passed through said plurality of conduits to control the temperature thereof.

15. The method as defined by claim 10 wherein said thermally-conductive block is made by a casting process in which molten metal is poured into a mold that is shaped to define said first and second cavities.

16. The method as defined by claim 10 wherein said thermally-conductive block is made by a casting process in which molten metal is poured into a mold that is shaped to define said first cavity, and wherein the shape of said second cavity is defined by independent conduits that are positioned within said mold during said casting process, said conduits being made of a second metal having a higher melting temperature than the metal from which said block is cast.

* * * * *